(12) United States Patent
Schmitt

(10) Patent No.: US 10,648,918 B2
(45) Date of Patent: May 12, 2020

(54) SYSTEMS, METHODS AND APPARATUS FOR DETERMINING A FRACTIONAL FLOW RESERVE (FFR) BASED ON THE MINIMUM LUMEN AREA (MLA) AND THE CONSTANT

(75) Inventor: Joseph Schmitt, Andover, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 1684 days.

(21) Appl. No.: 14/126,152

(22) PCT Filed: Aug. 1, 2012

(86) PCT No.: PCT/US2012/049122
§ 371 (c)(1),
(2), (4) Date: Aug. 7, 2014

(87) PCT Pub. No.: WO2013/019840
PCT Pub. Date: Feb. 7, 2013

(65) Prior Publication Data
US 2014/0379269 A1    Dec. 25, 2014

Related U.S. Application Data

(60) Provisional application No. 61/514,745, filed on Aug. 3, 2011.

(51) Int. Cl.
*G01N 21/85* (2006.01)
*A61B 5/00* (2006.01)
(Continued)

(52) U.S. Cl.
CPC ........... *G01N 21/85* (2013.01); *A61B 5/0066* (2013.01); *A61B 5/0084* (2013.01);
(Continued)

(58) Field of Classification Search
CPC ................ G01N 21/85; G01N 21/4795; A61B 5/02028; A61B 5/4836; A61B 5/489;
(Continued)

(56) References Cited

U.S. PATENT DOCUMENTS 5,085,223 A    2/1992  Lars et al.
5,125,058 A    6/1992  Tenerz et al.
(Continued)

FOREIGN PATENT DOCUMENTS

GB    2479340    10/2011
WO    01 54576    8/2001
(Continued)

OTHER PUBLICATIONS

Stefano et al. Utilization of frequency domain optical coherence tomography and fractional flow reserve to assess intermediate coronary artery stenoses: conciliating anatomic and physiologic information, Int J Cardiovasc Imaging 27:299-308, 2011.*
(Continued)

*Primary Examiner* — Serkan Akar
(74) *Attorney, Agent, or Firm* — K&L Gates LLP

(57) ABSTRACT

In one aspect, the invention relates to system comprising: a processor configured to receive a first optical coherence tomography (OCT) data set obtained during a pullback of a data collection probe along a first length of a first blood vessel; determine a minimum lumen area disposed along the first length using the first OCT data set; and determine a first FFR value along the first length based on the minimum lumen area. In one embodiment, the first FFR value is an estimated FFR. In another aspect, the invention relates to a method that includes measuring, using OCT, the area of a lumen of a vessel for which the vessel's FFR is to be determined; and calculating, using a computer, $A^2m/(A^2m+k)$ or $Y^{42}min/(Y^{42}min+k)$ as a FFR value. In one embodi-
(Continued)

ment, k is about 0.7 mm2 and γ is patient-specific variable that depends on the coronary branch in which the images were obtained.

13 Claims, 11 Drawing Sheets

(51) Int. Cl.
    *A61B 5/02*          (2006.01)
    *A61B 5/0215*       (2006.01)
    *G01B 9/02*          (2006.01)
    *G01N 21/47*        (2006.01)
    *A61B 34/10*        (2016.01)

(52) U.S. Cl.
    CPC ........ *A61B 5/02007* (2013.01); *A61B 5/0215* (2013.01); *A61B 5/02028* (2013.01); *A61B 5/489* (2013.01); *A61B 5/4836* (2013.01); *A61B 5/6852* (2013.01); *G01B 9/02091* (2013.01); *G01N 21/4795* (2013.01); *A61B 34/10* (2016.02); *A61B 2576/02* (2013.01)

(58) Field of Classification Search
    CPC . A61B 5/6852; A61B 5/0215; A61B 5/02007; A61B 5/0084; A61B 5/0066; A61B 34/10; A61B 2576/02; G01B 9/02091
    See application file for complete search history.

(56) References Cited

U.S. PATENT DOCUMENTS

| | | | |
|---|---|---|---|
| 5,195,375 A | 3/1993 | Tenerz et al. |
| 5,226,423 A | 7/1993 | Tenerz et al. |
| 5,307,811 A | 5/1994 | Sigwart et al. |
| 5,321,501 A | 6/1994 | Swanson et al. |
| 5,459,570 A | 10/1995 | Swanson et al. |
| 5,465,147 A | 11/1995 | Swanson |
| 5,509,093 A | 4/1996 | Miller et al. |
| 5,542,427 A | 8/1996 | Akerfeldt |
| 5,619,368 A | 4/1997 | Swanson |
| RE35,648 E | 11/1997 | Tenerz et al. |
| 5,694,946 A | 12/1997 | Tenerz et al. |
| 5,748,598 A | 5/1998 | Swanson et al. |
| 5,784,352 A | 7/1998 | Swanson et al. |
| 5,868,684 A | 2/1999 | Akerfeldt et al. |
| 5,873,835 A | 2/1999 | Hastings et al. |
| 5,938,624 A | 8/1999 | Akerfeldt |
| 5,965,355 A | 9/1999 | Swanson et al. |
| 6,089,103 A | 7/2000 | Smith |
| 6,090,052 A | 7/2000 | Akerfeldt et al. |
| 6,106,486 A | 8/2000 | Tenerz et al. |
| 6,111,645 A | 8/2000 | Tearney et al. |
| 6,112,598 A | 9/2000 | Tenerz et al. |
| 6,129,674 A | 10/2000 | Ovadia-Blechman |
| 6,134,003 A | 10/2000 | Tearney et al. |
| 6,142,958 A | 11/2000 | Hammarstrom et al. |
| 6,160,826 A | 12/2000 | Swanson et al. |
| 6,167,763 B1 | 1/2001 | Tenerz et al. |
| 6,182,513 B1 | 2/2001 | Stemme et al. |
| 6,191,862 B1 | 2/2001 | Swanson et al. |
| 6,196,980 B1 | 3/2001 | Akerfeldt et al. |
| 6,241,651 B1 | 6/2001 | Smith et al. |
| 6,248,083 B1 | 6/2001 | Smith et al. |
| 6,264,673 B1 | 7/2001 | Egnelov et al. |
| 6,282,011 B1 | 8/2001 | Tearney et al. |
| 6,312,380 B1 | 11/2001 | Hoek et al. |
| 6,336,906 B1 | 1/2002 | Hammarstrom et al. |
| 6,343,514 B1 | 2/2002 | Smith |
| 6,409,677 B1 | 6/2002 | Tulkki |
| 6,421,164 B2 | 7/2002 | Tearney et al. |
| 6,425,911 B1 | 7/2002 | Akerfelt et al. |
| 6,445,939 B1 | 9/2002 | Swanson et al. |
| 6,461,301 B2 | 10/2002 | Smith |
| 6,477,233 B1 | 11/2002 | Ribbing et al. |
| 6,485,413 B1 | 11/2002 | Boppart et al. |
| 6,501,551 B1 | 12/2002 | Tearney et al. |
| 6,503,266 B1 | 1/2003 | Sjogren et al. |
| 6,508,828 B1 | 1/2003 | Akerfeldt et al. |
| 6,517,481 B2 | 2/2003 | Hoek et al. |
| 6,546,804 B2 | 4/2003 | Stemme et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,596,012 B2 | 7/2003 | Akerfeldt et al. |
| 6,615,067 B2 | 9/2003 | Hoek et al. |
| 6,615,667 B2 | 9/2003 | Smith |
| 6,663,653 B2 | 12/2003 | Akerfeldt |
| 6,672,172 B2 | 1/2004 | Tulkki et al. |
| 6,682,489 B2 | 1/2004 | Tenerz et al. |
| 6,692,446 B2 | 2/2004 | Hoek |
| 6,706,004 B2 | 3/2004 | Tearney et al. |
| 6,712,837 B2 | 3/2004 | Akerfelt et al. |
| 6,754,608 B2 | 6/2004 | Svanerudh et al. |
| 6,786,915 B2 | 9/2004 | Akerfeldt et al. |
| 6,827,727 B2 | 12/2004 | Stalemark et al. |
| 6,860,895 B1 | 3/2005 | Akerfeldt et al. |
| 6,879,851 B2 | 4/2005 | McNamara et al. |
| 6,891,984 B2 | 5/2005 | Petersen et al. |
| 6,908,442 B2 | 6/2005 | von Malmborg et al. |
| 6,926,674 B2 | 8/2005 | Tenerz et al. |
| 6,929,655 B2 | 8/2005 | Egnelov et al. |
| 6,939,363 B2 | 9/2005 | Akerfeldt |
| 6,993,974 B2 | 2/2006 | Tenerz |
| 7,011,636 B2 | 3/2006 | Tenerz |
| 7,011,678 B2 | 3/2006 | Tenerz et al. |
| 7,021,152 B2 | 4/2006 | Tenerz |
| 7,044,916 B2 | 5/2006 | Tenerz |
| 7,073,509 B2 | 7/2006 | Tenerz |
| 7,094,209 B2 | 8/2006 | Egnelov et al. |
| 7,135,032 B2 | 11/2006 | Akerfeldt |
| 7,208,333 B2 | 4/2007 | Flanders et al. |
| 7,222,539 B2 | 5/2007 | Tulkki |
| 7,231,243 B2 | 6/2007 | Tearney et al. |
| 7,241,286 B2 | 7/2007 | Atlas |
| 7,263,894 B2 | 9/2007 | Tenerz |
| RE39,863 E | 10/2007 | Smith |
| 7,285,097 B2 | 10/2007 | Tenerz et al. |
| 7,326,088 B2 | 2/2008 | Tulkki |
| 7,329,270 B2 | 2/2008 | Akerfeldt et al. |
| 7,331,236 B2 | 2/2008 | Smith et al. |
| 7,343,811 B2 | 3/2008 | Tenerz et al. |
| 7,414,779 B2 | 8/2008 | Huber et al. |
| 7,415,049 B2 | 8/2008 | Flanders et al. |
| 7,445,625 B2 | 11/2008 | Akerfeldt |
| 7,450,989 B2 | 11/2008 | Svanerudh |
| 7,472,601 B1 | 12/2009 | Akerfeldt et al. |
| 7,625,366 B2 | 12/2009 | Atlas |
| 7,637,921 B2 | 12/2009 | Akerfeldt et al. |
| 7,645,233 B2 | 1/2010 | Tulkki et al. |
| 7,654,963 B2 | 2/2010 | Egnrlov et al. |
| 7,724,148 B2 | 5/2010 | Samuelsson et al. |
| 7,775,988 B2 | 8/2010 | Pijls |
| 7,775,992 B2 | 8/2010 | von Malmborg et al. |
| 7,813,609 B2 | 10/2010 | Petersen et al. |
| 7,848,791 B2 | 12/2010 | Schmitt et al. |
| 7,916,387 B2 | 3/2011 | Schmitt et al. |
| 7,931,603 B2 | 4/2011 | Von Malmborg et al. |
| 7,935,060 B2 | 5/2011 | Schmitt et al. |
| 7,938,846 B2 | 5/2011 | Akerfeldt et al. |
| 7,946,997 B2 | 5/2011 | Hubinette |
| 7,967,761 B2 | 6/2011 | Smith |
| 7,998,089 B2 | 8/2011 | Smith |
| 8,038,628 B2 | 10/2011 | von Malmborg et al. |
| 8,088,143 B2 | 1/2012 | Akerfeldt |
| 8,109,889 B2 | 2/2012 | von Malmborg et al. |
| 8,116,605 B2 | 2/2012 | Petersen et al. |
| 8,187,195 B2 | 5/2012 | Tulkki |
| 8,206,377 B2 | 6/2012 | Petroff |
| 8,216,151 B2 | 7/2012 | Smith |
| 8,308,758 B2 | 11/2012 | Akerfeldt |
| 8,323,215 B2 | 12/2012 | von Malmborg et al. |

(56) References Cited

U.S. PATENT DOCUMENTS

| | | | |
|---|---|---|---|
| 8,325,419 B2 | 12/2012 | Schmitt | |
| 8,358,461 B2 | 1/2013 | Huber et al. | |
| 8,398,675 B2 | 3/2013 | Egnelov | |
| 8,403,868 B2 | 3/2013 | Von Malmborg et al. | |
| 8,412,312 B2 | 4/2013 | Judell et al. | |
| 8,449,468 B2 | 5/2013 | Petersen et al. | |
| RE44,297 E | 6/2013 | Akerfeldt et al. | |
| 8,469,944 B2 | 6/2013 | Mahlin | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,579,825 B2 | 11/2013 | Tenerz et al. | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,641,633 B2 | 2/2014 | Smith | |
| 8,652,166 B2 | 2/2014 | Akerfeldt | |
| 8,687,201 B2 | 4/2014 | Adler | |
| 8,696,584 B2 | 4/2014 | Kassab | |
| 8,702,613 B2 | 4/2014 | Kassab | |
| 8,715,200 B2 | 5/2014 | Pijls | |
| 8,734,366 B2 | 5/2014 | Egnelov et al. | |
| 8,786,336 B1 | 7/2014 | Schmitt | |
| 8,802,124 B2 | 8/2014 | Tenerz et al. | |
| 8,831,321 B1 | 9/2014 | Elbasiony | |
| 8,948,228 B2 | 2/2015 | Adler | |
| 8,953,911 B1 | 2/2015 | Xu et al. | |
| 2002/0161351 A1 | 10/2002 | Samson et al. | |
| 2003/0216621 A1 | 11/2003 | Alpert et al. | |
| 2005/0201662 A1 | 9/2005 | Petersen et al. | |
| 2006/0009817 A1 | 1/2006 | Tulkki | |
| 2006/0052700 A1 | 3/2006 | Svanerudh | |
| 2006/0142786 A1 | 6/2006 | Mathisen et al. | |
| 2006/0161224 A1 | 7/2006 | Samuelsson et al. | |
| 2006/0205910 A1 | 9/2006 | Asplund et al. | |
| 2006/0211839 A1 | 9/2006 | Asplund et al. | |
| 2007/0255145 A1 | 11/2007 | Smith et al. | |
| 2007/0299542 A1 | 12/2007 | Mathisen et al. | |
| 2008/0077050 A1 | 3/2008 | Von Malmborg et al. | |
| 2008/0197750 A1 | 8/2008 | Katardjiev et al. | |
| 2008/0306494 A1 | 12/2008 | Magnusson et al. | |
| 2009/0030450 A1 | 1/2009 | Preinitz et al. | |
| 2009/0036920 A1 | 2/2009 | Preinitz et al. | |
| 2009/0069859 A1 | 3/2009 | Whinnett et al. | |
| 2009/0118643 A1 | 5/2009 | Smith et al. | |
| 2009/0174931 A1 | 7/2009 | Huber et al. | |
| 2009/0282437 A1 | 11/2009 | Malec et al. | |
| 2009/0306520 A1 | 12/2009 | Schmitt et al. | |
| 2010/0076320 A1 | 3/2010 | Petersen et al. | |
| 2010/0109104 A1 | 5/2010 | Tiensuu et al. | |
| 2010/0319345 A1 | 12/2010 | Sinan et al. | |
| 2011/0071404 A1 | 3/2011 | Schmitt et al. | |
| 2011/0071407 A1 | 3/2011 | Hubinette et al. | |
| 2011/0101207 A1 | 5/2011 | Schmitt | |
| 2011/0157686 A1 | 6/2011 | Huber et al. | |
| 2011/0190586 A1 | 8/2011 | Kemp | |
| 2011/0228280 A1 | 9/2011 | Schmitt et al. | |
| 2012/0101409 A1 | 4/2012 | von Malmborg et al. | |
| 2012/0310081 A1 | 6/2012 | Adler et al. | |
| 2012/0220898 A1 | 8/2012 | Tulkki | |
| 2012/0238869 A1 | 9/2012 | Schmitt et al. | |
| 2012/0250028 A1 | 10/2012 | Schmitt et al. | |
| 2012/0278008 A1 | 11/2012 | Davies et al. | |
| 2013/0010303 A1 | 1/2013 | Petersen et al. | |
| 2013/0012811 A1 | 1/2013 | Schmitt et al. | |
| 2013/0023761 A1 | 1/2013 | Petroff | |
| 2013/0046190 A1 | 2/2013 | Davies et al. | |
| 2013/0051728 A1 | 2/2013 | Petroff | |
| 2013/0072805 A1 | 3/2013 | Schmitt et al. | |
| 2013/0310698 A1 | 11/2013 | Judell et al. | |
| 2013/0345574 A1 | 12/2013 | Davies et al. | |
| 2014/0018669 A1 | 1/2014 | Xu | |
| 2014/0024931 A1 | 1/2014 | Winston et al. | |
| 2014/0039276 A1 | 2/2014 | Hattangadi et al. | |
| 2014/0094697 A1 | 4/2014 | Petroff et al. | |
| 2014/0114182 A1 | 4/2014 | Petersen et al. | |
| 2014/0135633 A1 | 5/2014 | Anderson et al. | |
| 2014/0136477 A1 | 5/2014 | Young et al. | |
| 2014/0142427 A1 | 5/2014 | Petroff | |
| 2014/0142432 A1 | 5/2014 | Hutchins et al. | |
| 2014/0142436 A1 | 5/2014 | Hutchins et al. | |
| 2014/0176554 A1 | 6/2014 | Cohen et al. | |
| 2014/0180035 A1 | 6/2014 | Anderson | |
| 2014/0180072 A1 | 6/2014 | Davies et al. | |
| 2014/0180140 A1 | 6/2014 | Alpert | |
| 2014/0180268 A1 | 6/2014 | Whiseant | |
| 2014/0180702 A1 | 6/2014 | Mansker et al. | |
| 2014/0180703 A1 | 6/2014 | Mansker et al. | |
| 2014/0180721 A1 | 6/2014 | Cheline et al. | |
| 2014/0181716 A1 | 6/2014 | Merritt et al. | |
| 2014/0181717 A1 | 6/2014 | Lahti et al. | |
| 2014/0187929 A1 | 7/2014 | Schmitt et al. | |
| 2014/0188503 A1 | 7/2014 | Balagnasay et al. | |
| 2014/0188513 A1 | 7/2014 | Balagnasay et al. | |
| 2014/0188514 A1 | 7/2014 | Balagnasay et al. | |
| 2014/0188515 A1 | 7/2014 | Mansker et al. | |
| 2014/0207008 A1 | 7/2014 | Davies et al. | |
| 2014/0218742 A1 | 8/2014 | Adler | |
| 2014/0236118 A1 | 8/2014 | Unser et al. | |
| 2014/0240713 A1 | 8/2014 | Kemp | |
| 2014/0249407 A1 | 9/2014 | Adler et al. | |
| 2014/0266577 A1 | 9/2014 | Anderson et al. | |
| 2014/0268167 A1 | 9/2014 | Friedman et al. | |
| 2014/0276011 A1 | 9/2014 | Schmitt et al. | |
| 2014/0276136 A1 | 9/2014 | Hattangadi et al. | |
| 2014/0276137 A1 | 9/2014 | Burnett et al. | |
| 2014/0276139 A1 | 9/2014 | Burkett et al. | |
| 2014/0276143 A1 | 9/2014 | Corl | |
| 2014/0276684 A1 | 9/2014 | Huennekens et al. | |
| 2014/0276687 A1 | 9/2014 | Goodman et al. | |
| 2014/0309536 A1 | 10/2014 | Douk et al. | |
| 2014/0379269 A1 | 12/2014 | Schmitt | |
| 2015/0025330 A1 | 1/2015 | Davies et al. | |
| 2015/0025398 A1 | 1/2015 | Davies et al. | |
| 2015/0080749 A1 | 3/2015 | Anderson et al. | |

FOREIGN PATENT DOCUMENTS

| | | |
|---|---|---|
| WO | 2012093266 | 7/2012 |
| WO | 2013028612 | 2/2013 |
| WO | 2013028613 | 2/2013 |

OTHER PUBLICATIONS

Takagi et al_Clinical Potential of Intravascular Ultrasound for Physiological Assessment of COronory Stenosis_Circulation, 1999; 100:250-255.*

Guagliumi et al., "Volumetric assessment of lesion severity with optical coherence tomography: relationship with fractional flow reserve", EuroIntervention 2013; 8: 1172-1181.

Parodi et al., "Patient-Specific Prediction of Coronary Plaque Growth From CTA Angiography: A Multiscale Model for Plaque Formation and Progression", IEEE Transactions on Information Technology in Biomedicine 16:5 Sep. 2012, pp. 952-965.

Taylor et al., "Computational Fluid Dynamics Applied to Cardiac Computed Tomography for Noninvasive Quantification of Fractional Flow Reserve", J Am Coll Cardiol 61:22, 2013 pp. 2233-2241.

Tonino et al., "Fractional Flow Reserve versus Angiography for Guiding Percutaneous Coronary Intervention", N Engl J Med 360:3, NEJM.org, Jan. 15, 2009 pp. 213-224.

Tu et al., "Fractional Flow Reserve Calculation From 3-Dimensional Quantitative Coronary Angiography and TIMI Frame Count a Fast Computer Model to Quantify the Functional Significance of Moderately Obstructed Coronary Arteries", JACC: Cardiovascular Interventions 7:7, Jul. 2014 pp. 768-777.

Volcano FFR Option Operator's Manual for Use with Volcano Imaging and Pressure Systems, Software Version Level 3.4.X, Apr. 2014 (64 pages).

(56) References Cited

OTHER PUBLICATIONS

Abe et al., "Diastolic Fractional Flow Reserve to Assess the Functional Severity of Moderate Coronary Artery Stenoses: Comparison with Fractional Flow Reserve and Coronary Flow Velocity Reserve", Circulation 2000; 102:2365-2370.

Brosh et al., "Pulse Transmission Coefficient: A Novel Nonhyperemic Parameter for Assessing the Physiological Significance of Coronary Artery Stenoses", JACC 39:6; 1012-9, Mar. 20, 2002.

Brosh et al., "Pulse Transmission Coefficient: A Novel Nonhyperemic Index for Physiologic Assessment of Procedural Success Following Percutaneous Coronary Interventions", Catherization and Cardiovascular Interventions 61:95-102 (2004).

Mamas et al., "Resting Pd/Pa Measured with Intracoronary Pressure Wire Strongly Predicts Fractional Flow Reserve", JIC invasivecardiology.com 22:6, 260-265 (Jun. 2010).

Marques et al., "The Diastolic Flow-pressure Gradient Relation in Coronary Stenoses in Humans", JACC 39:10, 1630-6, May 15, 2002.

Van der Horst, "Guidewire-mounted thermal sensors to assess coronary hemodynamics", ISBN: 978-90-386-3142-4, copyright 2012 by A. van der Horst, 174 pages.

Annex to Form PCT/ISA/206 of International Patent Application No. PCT/IB2015//000675 mailed Aug. 31, 2015 (5 pages).

International Search Report and Written Opinion of the International Search Authority dated Nov. 2, 2012 for International Application N. PCT/US2012/049122 (7 pages).

\* cited by examiner $$FFR_{pred} = \frac{A^2_{min}}{A^2_{min} + k}$$

WHERE
$$k = A^2_{ref}\left(\frac{1}{FFR_{ref}} - 1\right) = 0.683\ mm^2$$

FOR $FFR_{ref} = 0.75$ AND $A^2_{ref} = 1.43\ mm^2$

US 10,648,918 B2

SYSTEMS, METHODS AND APPARATUS FOR DETERMINING A FRACTIONAL FLOW RESERVE (FFR) BASED ON THE MINIMUM LUMEN AREA (MLA) AND THE CONSTANT

CROSS REFERENCE TO RELATED APPLICATIONS

This application is a national phase under 35 U.S.C. § 371 of International Application No. PCT/US2012/049122 filed on Aug. 1, 2012, which claims priority to and the benefit of U.S. Provisional Patent Application No. 61/514,745, filed on Aug. 3, 2011, the entire disclosures of which is are herein incorporated by reference.

FIELD OF THE INVENTION

In part, the invention relates to methods, systems and devices suitable for directly or indirectly determining certain parameters, such as areas and flow reserves using blood vessel measurements obtained using optical coherence tomography.

BACKGROUND OF THE INVENTION

Coronary artery disease is one of the leading causes of death worldwide. The ability to better diagnose, monitor, and treat coronary artery diseases can be of life saving importance. The decision to place a stent in a coronary artery depends on the amount of occlusion of the artery by a plaque, which is most often assessed by angiography according to quantitative measures of vessel stenosis, such as the minimum lumen area (MLA) and percent area stenosis (% AS). The relationship of these geometric measurements to ability of the artery to supply an adequate flow of blood to the myocardium when metabolic demands are high has been a long-standing area of investigation.

The relevance of the minimum lumen area (MLA) as a measure of lesion severity has been debated by experts and prior attempts to use it have not been compelling. For example, attempts to relate MLA and Fractional Flow Reserve (FFR), a standard measure of the physiological significance of a lesion, by simple linear regression and curve fitting of experimental data have achieved little success. Others are developing sophisticated 3D flow models, to predict FFR from magnetic resonance (MR) angiograms. Several significant factors appear to limit standard angiography from predicting FFR from MLA measurements.

First, the accuracy and reproducibility with which cross-sectional areas can be measured with angiography, which generally has a spatial resolution of 0.2-0.4 mm, are relatively low. The angle of the X-ray projection, in addition to the shadowing effect of lesions with irregular contours, can increase errors significantly beyond the theoretical minimums.

Second, when assessing the physiological significance of a lesion and the potential value of revascularization, it is important to account for the normal dimensions of the vessel as well as the minimum cross-sectional area at the site of the lesion. These variables influence the blood flow through the lesion and, hence, the magnitude of the pressure drop caused by a given MLA value.

Third, the hemodynamic effects of a lesion depend on local variations of its cross-sectional area integrated over the entire length of a lesion. Therefore, the minimum cross sectional area alone is insufficient to characterize the pressure drop across a lesion at a given flow rate, especially in patients with diffuse coronary disease.

Fourth, the flow resistance or pressure drop caused by an incremental segment of a lesion depends on its shape as well as its cross-sectional area and length. Especially at high blood flow rates, the eccentricity and local slope of the walls of the artery can influence the effective resistance of a lesion, because losses due to flow separation and turbulence depend on local flow velocity.

Finally, in certain patients, the flow reserve of the myocardium supplied by the vessel can be low, due to microvascular disease, flow through collateral branches, or capillary shunts within infarcted myocardium. Therefore, even if the vascular resistance of a lesion in the vessel is high, revascularization may be contraindicated, because the pressure drop across the lesion may be clinically insignificant.

Optical coherence tomography (OCT) imaging, applied in combination with new clinical parameters based on advanced analysis of lesion morphology, has the potential to overcome many of the limitations of conventional measures of lesion severity based on angiography. Intravascular optical coherence tomography (OCT) is a catheter-based imaging modality that employs safe, non-ionizing near-infrared light to peer into coronary artery walls and present images valuable for the study of the vascular wall architecture. Utilizing broad-band coherent light, interferometry, and micro-optics, OCT can provide video-rate in-vivo tomography within a diseased vessel with resolution down to the micrometer level. This level of detail enables OCT to diagnose as well as monitor the progression of coronary artery disease.

The high resolution of OCT enables accurate measurement of the shape and dimensions of the vessel lumen over the length of the lesion and its adjacent reference segments. Furthermore, advanced models of flow dynamics enable the physiological significance of lesions to be estimated under both normal and hyperemic conditions. The accuracy of OCT even exceeds that of state-of-the-art IVUS imaging systems, which have resolutions of approximately 0.15 mm in the axial dimension and 0.3 mm in the angular dimension. Because static blood obscures the boundaries of tight lesions, IVUS is limited in its ability to accurately measure MLA values below about 1-2 mm$^2$. Given all of the problems relating to existing attempts to measure FFR, a need therefore exists for accurate methods of determining or measuring FFR and other cardiovascular system related processes, and devices.

The present invention addresses this need and others.

SUMMARY OF THE INVENTION

In part, the invention relates generally methods, devices and systems for determining FFR to aid in diagnosing and otherwise obtaining additional data with respect to a given vessel that uses MLA and other parameters in conjunction with one or more computational models to determine FFR. Specifically, in one embodiment, the invention relates to a method of relating geometrical measurements of a blood vessel such as the MLA of the blood vessel with the FFR for the same blood vessel based on blood vessel type and a reference FFR value. The method accounts for the effect of branch-dependent hyperemic resistance and the inverse square-law dependence of vessel area and stenotic resistance. In one embodiment, MLA and FFR are types of patient parameters that are generated in response to or derived from OCT data directly, such as in the case of a measured MLA value, and indirectly, such as a FFR value that is generated or determined using a measured MLA value obtained from OCT data and a computational model.

In one aspect, the invention relates to an optical coherence tomography system. The system includes a data collection probe configured to receive light scattered from a vascular lumen; a detector configured to receive the scattered light from the vascular lumen and convert the received light into an electrical signal; a memory configured to store a software-based model, the software-based model configured to generate an estimated FFR value based on a minimum lumen area (MLA) value; and a processor configured to: generate a plurality of images based on the electrical signal, each image corresponding to a cross-section of the vascular lumen along a length of the vascular lumen; determine a luminal border for one or more of the plurality of images; determine the MLA value along the length of the vascular lumen; and determine the estimated FFR value in response to the MLA value and the software-based model. In one embodiment, the software-based model determines the estimated FFR using the following relationship: estimated FFR=(MLA value)$^2$/[(MLA value)$^2$ k].

In one embodiment, k ranges from about 0.5 mm$^2$ to about 2 mm$^2$. In one embodiment, k ranges from about 0.5 mm$^2$ to about 0.7 mm$^2$ In one embodiment, the software-based model determines the estimated FFR using the following relationship: estimated FFR=[γ(MLA value)$^2$]/[γ(MLA value)$^2$ k], wherein γ is a vascular lumen type specific parameter. In one embodiment, γ ranges from about 1.0 mm$^2$ to about 2.0 mm$^2$. In one embodiment, wherein the processor is further configured to generate an output that indicates a stent is recommended for insertion in the vascular lumen if the estimated FFR value is about 0.80 or less. In one embodiment, if the vascular lumen already has a stent disposed therein, the processor is further configured to generate an output that indicates a corrective procedure is recommended if the estimated FFR value is about 0.80 or less. In one embodiment, the processor is further configured to generate an output that indicates a stenotic lesion is present in the vascular lumen if the estimated FFR value is about 0.80 or less.

In one embodiment, the software-based model is configured to output an estimated FFR value derived from the MLA value, wherein the software-based model is configured based on a plurality of conditions which include: hyperemic flow is approximately constant; a ratio of D/L is approximately constant, wherein L is the length of a stenotic lesion and D is a diameter of the vascular lumen outside of the stenotic lesion; and A$^2$/(MLA value)$^2$>1, wherein A is an area of the vascular lumen outside of the stenotic lesion. In one embodiment, the software-based model is configured to output an estimated FFR value in response to the MLA value, wherein the software-based model is configured such that resistance to flow in a stenosis in the vascular lumen is about k/(MLA value)$^2$.

In one aspect, the invention relates to a processor-based method of determining an estimated FFR. The method includes collecting OCT data from a lumen of a blood vessel while pulling an OCT probe through the lumen; determining, using a processor, a location of a stenotic lesion in the blood vessel; determining, using the processor, the MLA at the location of minimum lumen diameter at the stenotic lesion location; and calculating, using the processor and a software-based model, the estimated FFR, wherein the software-based model is a function of the MLA and a constant.

In one embodiment, the constant is empirically determined and describes an error value. In one embodiment, the software-based model determines the estimated FFR using the following relationship: estimated FFR=(MLA value)$^2$/ [(MLA value)$^2$ k]. In one embodiment, k ranges from about 0.5 mm$^2$ to about 0.7 mm$^2$ In one embodiment, the software-based model determines the estimated FFR using the following relationship: estimated FFR=[γ(MLA value)$^2$]/[γ (MLA value)$^2$+k], wherein γ is a blood vessel type specific parameter. In one embodiment, the method further includes the steps of: generating a plurality of images based on the OCT data, each image corresponding to a cross-section of the blood vessel; and determining a luminal border for one or more of the plurality of images, wherein the MLA is determined using the luminal border.

In one embodiment, the method further includes the step of configuring the software-based model such that hyperemic flow is approximately constant; a ratio of D/L is approximately constant, wherein L is the length of a stenotic lesion and D is a diameter of the blood vessel outside of the stenotic lesion; and A$^2$/(MLA value)$^2$>1, wherein A is an area of the blood vessel outside of the stenotic lesion. In one embodiment, the software-based model is configured such that resistance to flow in the stenotic lesion in the blood vessel is about k/(MLA value)$^2$. In one embodiment, the processor is further configured to generate an output that indicates a stenotic lesion is present in the blood vessel if the estimated FFR is about 0.80 or less. In one embodiment, γ ranges from about 1.0 mm$^2$ to about 2.0 mm$^2$.

In one aspect, the invention relates to system that includes a processor configured to receive a first OCT data set obtained during a pullback of a data collection probe along a first length of a first blood vessel; determine a minimum lumen area disposed along the first length using the first OCT data set; and determine a first FFR value along the first length based on the minimum lumen area. In one embodiment, the first FFR value is an estimated FFR. In one embodiment, the method further includes the step of applying a correction factor which is dependent upon the type of vessel. In one example, such a correction factor is denoted by γ. k is an example designation of an empirically determined constant that can be used to related stenotic resistance to a MLA value or the square of a MLA value as part of a software model using OCT data as an input. In one embodiment, the processor is further configured to identify a luminal border on a per frame basis. In one embodiment, the first OCT data set includes a plurality of frames, wherein each frame includes a cross-sectional image generated during the pullback from which a processor determines a MLA value.

A computer-based system configured to process OCT data that includes a OCT data acquisition system for collecting images in situ of a region of a lumen; a memory storing the images; and a processor in communication with the memory, the processor configured to perform one or more of the following: increase a correlation level between a set of measured FFR values and a predicted FFR value, generate a k value on a per blood vessel basis using OCT data for such a vessel and one or more parameters, linearize a first multivariate function to obtain a second multivariate function having a reduce error level, wherein one variable of each of the first and second functions is MLA and the output of the first and second functions is a FFR value. In one embodiment, the plurality of images is OCT images and the image acquisition system comprises an interferometer and a catheter for collecting in-situ vascular images. The catheter has a rotatable optical fiber disposed therein.

In one aspect, the invention relates to a method of determining FFR that includes measuring, using OCT, the cross-sectional area of a lumen of a vessel for which the vessel's FFR is to be determined; and calculating, using a computer, the relationship: $FFR_{estimated} = A^2_m/(A^2_m+k)$, wherein k is about 0.7 mm² and $A_m$ is the minimum lumen area of the vessel. A plurality of cross-sectional areas is measured in one embodiment. In one embodiment k is about 0.683 mm². MLA and $A_m$ are used interchangeably and "area" and "cross-sectional area" are used interchangeably while also retaining their ordinary meaning.

In another aspect, the invention relates to a method of determining FFR comprising the steps of measuring, using OCT, the cross-sectional area of a lumen of a vessel for which the vessel's FFR is to be determined; and calculating, using a computer, the relationship: $FFR_{estimated} = \gamma A^2_m/(\gamma A^2_m+k)$ wherein k is a constant in the range of about 0.5-about 2.0 mm² and γ is a correction factor for various types of vessels. In one embodiment, k is about 0.683 mm². In one embodiment, each cross-sectional area has a radial error that ranges from about 0.02 mm to about 0.4 mm. This range is desirable because diameters errors greater than about 0.2 mm yield unacceptably large FFR errors.

In yet another aspect, the invention relates to an apparatus for determining FFR comprising an OCT device, the OCT device measuring the cross-sectional area of a lumen of a vessel for which the vessel's FFR is to be determined; and a processor in communication with the OCT device, the processor calculating, the relationship: $FFR_{estimated} = A^2_m/(A^2_m+k)$ wherein k is in the range from about 0.5 mm² to about 2.0 mm² In one embodiment, k is about 0.683 mm².

In still yet another embodiment, the invention relates to an apparatus for determining FFR comprising an OCT device, the OCT device measuring the cross-sectional area of a lumen of a vessel for which the vessel's FFR is to be determined; and a processor in communication with the OCT device, the processor calculating, the relationship: $FFR_{estimated} = \gamma A^2_{min}/(\gamma A^2_{min}+k)$. γ is a correction factor that can be determined with respect to various blood vessels such as different coronary arteries.

In yet another aspect, the invention relates to an optical coherence tomography data collection system. The system includes a memory configured to store one or parameters; and a processor configured to receive a first OCT data set obtained during a pullback of a data collection probe along a first length of a first blood vessel; determine a minimum lumen area disposed along the first length using the first OCT data set; and determine a first FFR value along the first length based on the minimum lumen area. In one embodiment, the first FFR value=$A^2_m/(A^2_m+k)$. In one embodiment, the parameter is blood-vessel type specific correction factor.

DETAILED DESCRIPTION

Figure 1A:
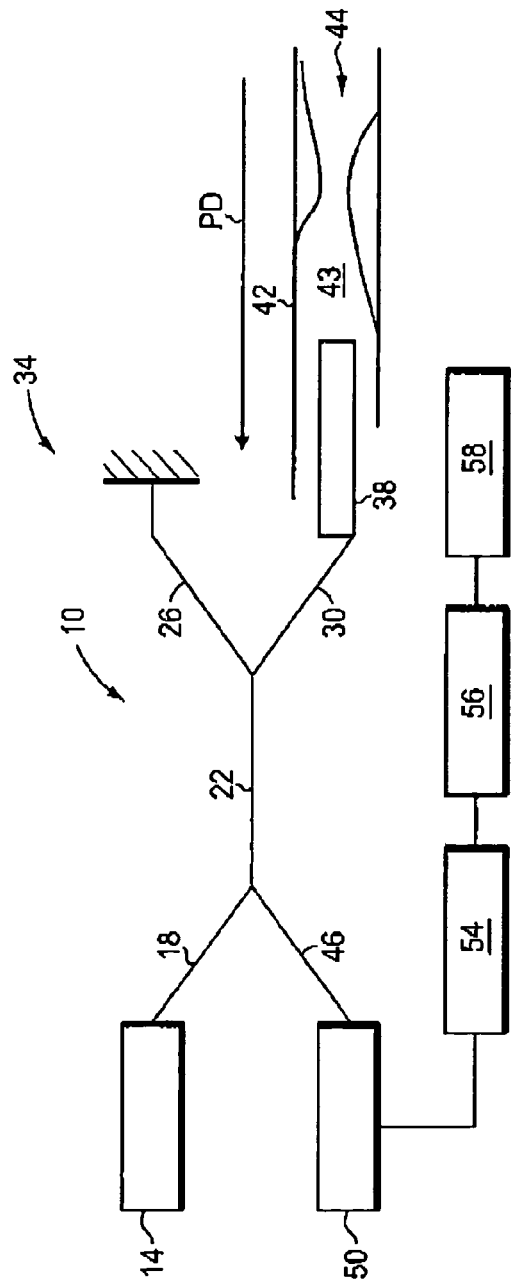
FIG. 1A is a schematic diagram of a generalized system for making a FFR measurement using minimum lumen area according to an illustrative embodiment of the invention.

In part, the invention relates to systems, method and apparatuses that can determine, generate or evaluate a fractional flow reserve ("FFR") value such as a measured, estimated, modeled or approximated FFR value using a minimum lumen area ("MLA") value such as a measured, estimated, modeled or approximated MLA value. Specifically, a MLA value can be obtained by interferometrically measuring a blood vessel and processing one or more OCT data sets that include a stenotic region and regions to either side of such as stenotic region. Accordingly, in one embodiment, a FFR value is obtained using an optical data collection method and system instead of a pressure data collection method and system. In the field of interventional cardiology, parameters such as MLA and FFR values are used to assess blood vessel conditions and cardiovascular performance. These values can be determined using pressure sensors, angiography, MRI, and other data collection modalities.

In part, one embodiment of the invention provides an approximate method that improves the accuracy of FFR predictions without acquiring pressure data using a pressure probe or modeling flow in three-dimensional models of the coronary arteries. The method estimates FFR from MLA measurements, supplemented by additional patient-specific information, at an error level that allows the resultant estimated FFR values to be used to decision making purposes such as to insert a stent in a blood vessel or replace an existing stent. In one embodiment, the terms predicted FFR and estimated FFR are used interchangeably.

In one embodiment, the invention describes one or more computer implemented models that receive an optical coherence tomography data set acquired during a pullback with respect to a blood vessel of a subject as inputs. This data set can include image data such as cross-sectional images of a lumen, data extracted from such images, or other data obtained using an OCT data collection probe disposed in the applicable blood vessel. The OCT data set acquired with respect to a particular blood vessel can be used to accurately measure the MLA for the blood vessel. In turn, such a measured MLA can be operated upon or transformed using a model implemented in software executing on a processor to generate a FFR value.

This process, the underlying model and inputs necessary to determine such an FFR value are complicated by the non-linearity of the relationship between MLA and FFR. In part, the non-linearity is thought to occur as a result of the degree of stenosis exhibiting a non-linear relationship relative to how the stenosis changes blood flow in a vessel. For example, changes in lumen area for a stenotic lesion may result in significant changes to blood flow once a certain threshold level of narrowing has occurred, but exhibit less of an impact on blood flow, and thus FFR, if the level of stenosis is below such a threshold.

In part, the process of designing a software-based model to transform OCT data into a measured MLA value and subsequently or substantially simultaneously transform the measured MLA value into a FFR value, requires various considerations and constraints. For example, identifying data or specific parameters to give a low or zero weight as a component of the model and other parameters that have a higher or non-zero weight in the model are important factors in terms of producing accurate FFR values using distance or area measurements. Specifically, various simplifying assumptions are included herein that specify constraints such as one value being significantly larger than another parameter's value, which parameters are emphasized and other factors identified to generate a predicted FFR. In addition, being able to simplify the processing steps of the model while generating a FFR value that can be used to inform decision making such as whether or not to stent is advantageous. The software-based model can also include certain other inputs and steps such as characterizing a blood vessel to identify its type and using such s blood vessel type as a further input in the FFR determining model.

For a given blood vessel, a relationship between MLA and FFR such as a curve or data set identified by graphing such values depends, to some extent, on various parameters and factors. These parameters and factors can vary on a per blood vessel basis. An exemplary list of such variables and factors includes, without limitation, reference diameters of the vessel, number of lesions, lesion length/diffusivity, size and location of side branches, and minimum microvascular resistance under hyperemia. One embodiment of the model outline herein directly or indirectly use or are constrained by one or more of these parameters and factors. Prior to considering the methods and models relating to FFR, it is useful to consider an OCT system used to collect the blood vessel specific data that is used as an input to such methods and models.

Figure 1B:
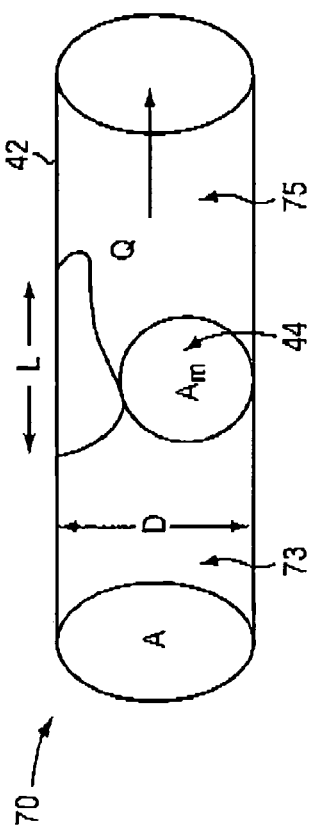
FIG. 1B is a schematic diagram of the geometry of a vessel with a stenotic lesion according to an illustrative embodiment of the invention.

In brief overview and referring to FIG. 1A, a generalized OCT system 10 is shown which is suitable for use with the OCT data collection probes of the invention to determine a FFR value from a measured MLA value. The OCT probes and system 10 collect data that can be used to generate an image of the blood vessel such as shown in FIG. 1D. A light source 14, such as a laser, produces light that passes by way of an optical fiber 18 into an optical fiber coupler 22. Light entering the coupler 22 is the split along two optical fiber paths 26 and 30. Light along one path 26 terminates at a reference reflector 34. This path 26 is part of the reference arm of an interferometer. In turn, the light transmitted along the path 30 enters a data probe 38 located within a blood vessel. The data collection probe can be an OCT probe and includes a rotatable optical fiber having a beam director in optical communication therewith. The light in a sample arm of the interferometer, which includes path 30, propagates toward the wall 42 of the blood vessel.

Since the optical fiber in probe 38 rotates, depth information can be generated using interferometry with respect to cross-sections of the wall 42. The blood vessel includes a lumen 43 in which blood flows and an abnormal narrowing also referred to as a stenosis 44 in one embodiment. The probe 38 can be pulled back from a position ahead of the stenosis 44 such that OCT data is collected with respect to the stenosis 44 and regions of the wall 42 on either side of the stenosis. For example, the probe 38 can be positioned beyond stenosis 44 and pulled back along a length of the blood vessel corresponding to a pullback distance PD. The blood vessel can be any suitable blood vessel such as for example a coronary artery, including without limitation the left anterior descending artery, left circumflex artery, or the right coronary artery.

Light reflected by the reflector 34 passes back along optical fiber 26 to the coupler 22. Similarly light reflected by the wall of the vessel 42 passes back along optical fiber 30 to the coupler 22 and combines with the light reflected by the reflector 34 to form an interference pattern. This combined light passes through optical fiber 46 and is detected by a detector 50 such as photodiode or electro-optical converter. The output signal from the detector 50 is processed by electronics 54, such as photodiodes, filters, and other components. The output signal or a processed version thereof is processed or transformed by the processor 56 to form one or more images of the vessel wall on the display 58. A longitudinal view of the wall 42 and substantially circular or elliptical cross-sections of the wall 42 can be generated and viewed on the display 58.

The processor 56 can be used to generate various values and parameters relative to the blood vessel being imaged using software applications, hardware, or other circuits configured to run models such as OCT data dependent models described herein to generate predicted FFR values. The processor 56 can also be configured to respond to various signals and thresholds to provide modified data for such models, to run such models or otherwise generate or determine information of interest relative to the blood vessel such as FFR values and MLA values. In this way, a plurality of interferometric measurements can be obtained to generate an OCT data set that includes images and cross-sectional areas of a blood vessel from which a processor can run one or more software applications or models to generate a minimum lumen area based on the OCT data set. A FFR value such as a predicted FFR can be determined using the minimum lumen area and other information including but not limited to the OCT data set or other data derived therefrom.

In one embodiment, the calculations and transformation of patient data such as image data and vessel distance measurements are performed by the processor 56 or another processor or control system used with the overall data collection system. In one embodiment, the processor receives information from a physician or physician assistant for determination of the vessel-dependent parameter γ as described herein. Such information may include, for example, the branch of the artery that contains the lesion or patient characteristics such as weight, age, height, and body mass index (shown generally as m in FIG. 1C). Various inputs for a given model to obtain a predicted FFR are shown in FIG. 1C.

Figure 1C:
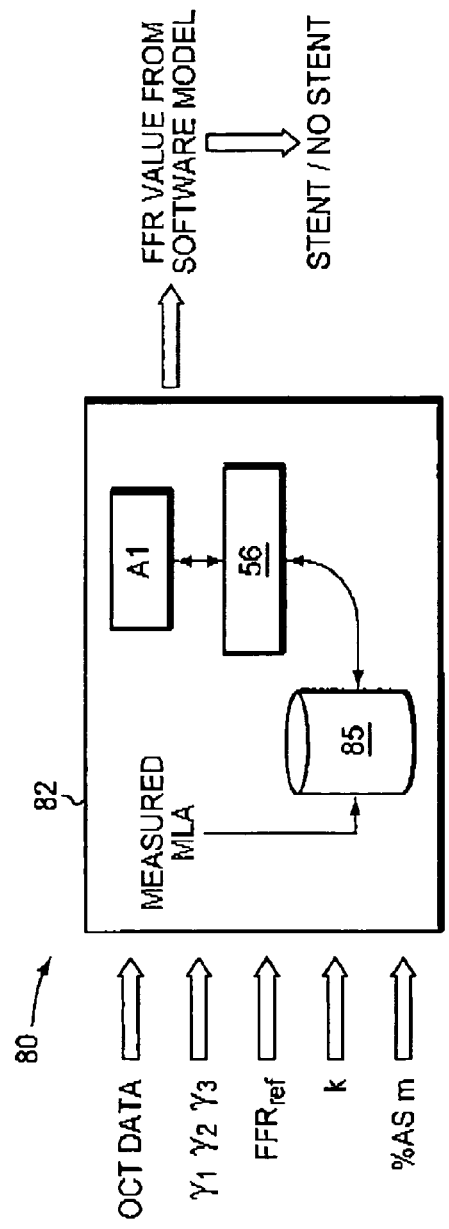
FIG. 1C is a schematic of a processor-based system that includes a computational model that receives one or more OCT data sets and other parameters as inputs and generates an estimated FFR value as an output according to an illustrative embodiment of the invention.
Figure 1D:
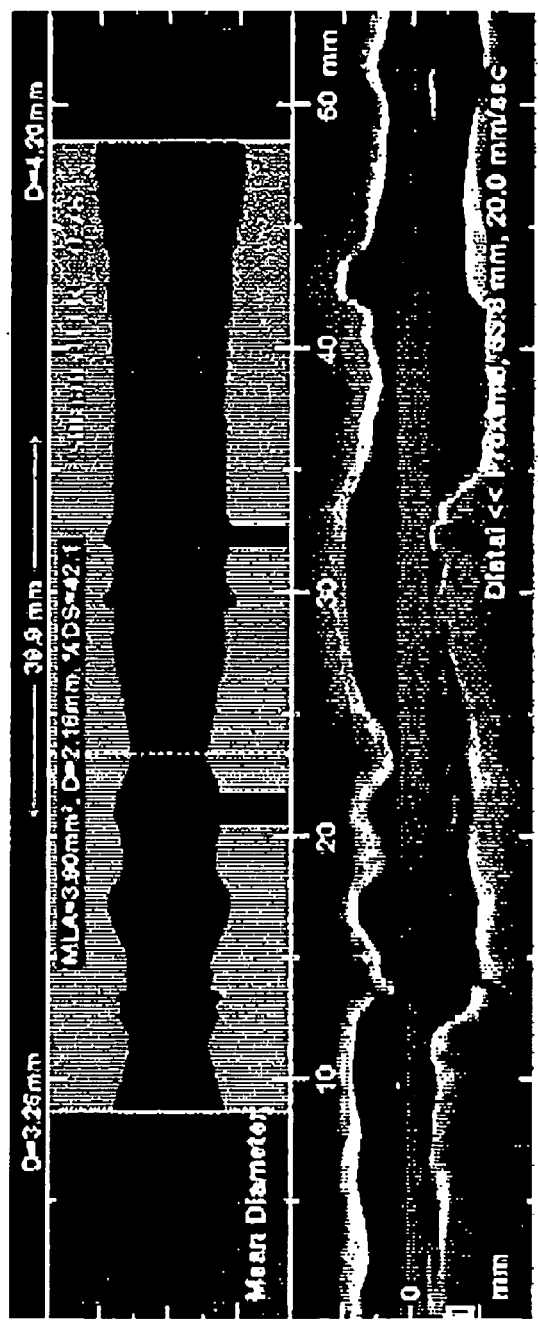
FIG. 1D is a screenshot of a user interface screen displaying a blood vessel image generated using OCT data that includes an estimated FFR value according to an illustrative embodiment of the invention.

In FIG. 1C, a system 80 configured to receive various blood vessel specific and other relevant parameters as inputs that can be received by the relevant channel such that the parameters can be operated upon by processor 56. A general interface layer 82 is shown to represent the different channels by which the input parameters on the right side of system 80 can be received and operated upon by the processor 56 or stored in volatile or nonvolatile memory such as for example a datastore or memory 85. A measured MLA from the OCT data is stored in memory 85 in one embodiment. The datastore or memory 85 is accessible by the processor 56. In one embodiment, inputs are provided to the model through manual operator entry or automatically via a hospital or other facility's DICOM network.

The model, which can include one or more equations described herein, can be implemented as a software application A1. The equations and processing steps described herein that generate some of the parameters on the left side of FIG. 1C are outlined below. The processor can be configured to run a software application A1 that includes one or more models and generate a predicted FFR value as well as provide a recommendation such as whether or not inserting a stent in the blood vessel is recommended. This information can be displayed using display 58. If a stent is already in the blood vessel, other corrective action such as another procedure, stent removal, or repositioning the stent can be provided to a user.

The processor 56 can be used to generate various values and parameters relative to the blood vessel being imaged using software applications, hardware, or other circuits configured to run models such as OCT data dependent models. The processor 56 can also be configured to respond to various control signals and thresholds to provide modified data for such models, to run such models or otherwise generate or determine information of interest relative to the blood vessel such as FFR values and MLA values. The processor 56 can be part of a computer system. Alternatively, the processor can be a plurality of circuits or a component of a control system.

In one embodiment, the calculations and transformation of patient data such as image data and vessel distance measurements are performed by the processor 56 or another processor or control system used with the overall data collection system. In one embodiment, the processor receives information from a physician or physician assistant for determination of the vessel-dependent parameter γ as described herein. Such information may include, for example, the branch of the artery that contains the lesion or patient characteristics such as weight, age, height, and body mass index.

In one embodiment, an FFR value such as a predicted FFR is calculated by using OCT such as with a data collection probe 38 of FIG. 1A to measure the minimum lumen area in a particular blood vessel such as an artery of interest. In a full Vascular Resistance Ratio (VRR) model, VRR=$R_s/R_T$, where $R_s$ is the resistance to flow in the stenotic portion of the vessel and $R_T$ is the total flow resistance of the vessel. The stenotic resistance, $R_s$ of a single stenotic narrowing with a minimum lumen area (MLA), $A_m$, can be modeled as a sum of three fluid resistance terms, with subscripts 'p', 'v', and 'e' as shown in equation 1:

$$R_s = \Delta P/Q = R_p + R_v + QR_e \quad (1)$$

The three resistive terms represent the Poiseuille losses ($R_p$), excess viscous entrance losses ($R_v$), and Bernoulli expansion (also sometimes called "momentum") losses ($R_e$), respectively. As shown in equation 1, ΔP is the mean pressure applied across the stenotic lesion, which is assumed to be a constant equal to the difference between the mean arterial and venous pressures. Q is the blood flow through the lesion. All three types of losses vary in inverse proportion to the square of the MLA or $A_m$:

$$R_p = k_1 L/A_m^2 \quad (2)$$

$$R_v = k_2 D/A_m^2 \quad (3)$$

$$R_e = k_3 (1/A_m^2 - 1/A^2) \quad (4)$$

wherein (see FIG. 1B) $k_1$, $k_2$, and $k_3$ are constants related to the properties of the blood; L is the length of the stenotic lesion; D and A are the diameter and area of the vessel outside of the stenosis, respectively. A computational model that can be implemented using software as part of an OCT data collection system can be configured using the following assumptions:

1. that the hyperemic flow, $Q_{hyp}$, is approximately constant for a given vessel:

$$Q = Q_{hyp=constant}; \quad (5) \text{ and}$$

2. that the stenotic lesions are tight and short, with:

$$D/L \approx constant, \text{ and} \quad (6)$$

$$A^2/A_m^2 \gg 1 \quad (7)$$

Then:

$$R_s = k/A_m^2 \quad (8)$$

with the constant k determined empirically by curve fitting to obtain the smallest mean-squared error (or an equivalent quality-of-fit measure) from measurements of FFR and MLA on a large population of patients. In one embodiment, k ranges from between about 0.5 mm² to about 2 mm² Now the predicted FRR ($FRR_{pred}$) for an unbranched arterial segment with a single stenotic region is given by the expression:

$$FRR_{pred} = 1 - (R_s/(R+R_s)) = R/(R+R_s) \quad (9)$$

where $R_s$ is the stenotic resistance and R is the hyperemic microvascular resistance. From equation 8, $$FRR_{pred} = R/(R+(k/A_m^2)) \quad (10)$$

Or, assuming R remains constant for vessels with different MLAs:

$$FFR_{pred} = A_m^2/(A_m^2 k) \quad (11)$$

In one embodiment, k is about 0.683 mm².

In another embodiment, the predicted FFR is calculated by applying a correction factor (γ) which is dependent upon the type of vessel:

$$FFR_{pred}=\gamma A^2_m(\gamma A^2_m+k) \quad (12)$$

The value of k can be any of the values specified herein or as may be determined applicable to a given data collection session. In addition, in one embodiment γ takes the following values depending upon which coronary artery is being treated:

γ=1.00 for LAD (Left anterior descending artery)  (13)

γ=1.66 for LCX (Left Circumflex artery),  (13)

γ=1.20 for RCA (Right coronary artery)  (13)

The above-referenced γ values are provided as non-limiting examples. In addition, γ need not be limited to the arteries referenced above, but can be generalized to other blood vessels including smaller arterial branches. In one embodiment, γ ranges from about 1.0 mm² to about 2.0 mm².

These values correspond to the relative hyperemic resistances of the main coronary branches, determined from ratio of the mean blood flow rates in each branch, that have been published in the academic literature (see, e.g., Mittal et al, Am J Physiol Heart CircPhysiol 289; H439-H446, 2005). Other values of γ can be determined by trial and error from experimental results to provide a functional relationship between MLA and FFR that applies to a broader population of patients. If the type of artery is not available as an input, the values of γ can also be estimated in one embodiment from the percent area stenosis (% AS) or diameter stenosis (% DS) values measured from OCT or angiographic images of the artery of interest. The value of γ decreases in proportion to the diameter of the unstenosed segment of the artery. In one embodiment, the hyperemic microvascular resistance associated with a stenosis depends not only on the specific type of artery in which the stenosis is located, as accounted for by the applicable γ value, but also on the myocardial mass fed by the artery. In one embodiment, other patient parameters that influence the size of the heart or the artery (e.g., angiographic reference diameters used in the calculation of area or diameter stenosis) can be used as additional inputs for determination of γ.

Therefore, more generally,

γ=ƒ(artery type,patient-specific variables)  (14)

where ƒ denote a multivariate "function of" artery types and patient-specific variables. The functional relationship for γ and the patient-specific variables are normally stored on the OCT system such as in memory 85 as part of the patient record, so the processor 56 automatically has access to this information. In accordance to practices known to those skilled in the art, a patient-specific adjustment to the constants in Eq 13 can be determined by a multiple regression from a group of paired MLA and FFR measurements, with the least-mean-squared error serving as the fit criterion.

Referring to FIGS. 1A and 1B, in operation, a system 10 configured to collect blood vessel specific data OCT data collection probe 38 is inserted into the blood vessel of interest and the wall 42 of the lumen of the vessel is determined by techniques known by one skilled in the art. Once the lumen wall 42 is detected, the area of the lumen such as the cross-sectional lumen area in stenosed regions such as region 44 and non-stenosed regions such as regions 73 and 75 is determined using the processor 56 or other devices and system components. In one embodiment, once the MLA is determined, the system 10 applies the desired equation for the blood vessel in question using the processor 56 and displays the FFR on display 58.

The lumen wall 42 also referred to a luminal border can be determined using an OCT data collection probe and other components of the OCT system. The probe scans a blood vessel as it rotates such that depth information can be generated using interferometric principles. This depth information can be used to generate a plurality of cross-sectional images of the blood vessel having the lumen and lumen wall 42. These images can be stored in memory for subsequent processing. In one embodiment, the processor is configured to generate a mask of the image; define a plurality of scan lines in said mask; identify a region as tissue on each scan line; define contour segments in response to the plurality of scan lines and the region of tissue on each scan line; identify valid neighboring contour segments; interpolate missing contour data between valid neighboring contour segments; and fit a contour to the missing contour data. This is one such way for the luminal border to be identified, which can be used to identify lumen areas on a per frame basis which can be evaluated to determine the MLA.

FIG. 1D is a screen shot of an image of a blood vessel 100 such as can be shown using display 58 in accordance with an embodiment of the invention. This image of the blood vessel 100 generated using OCT data is part of a user interface screen in one embodiment. The bottom portion of the image 100 is the longitudinal view of the blood vessel. The top portion of the image 100 is a longitudinal view with additional parameters identified. The MLA value of 3.90 mm² is shown by the dotted line near the middle of the image 100. Various diameters of the blood vessel including the diameter (2.16 mm) associated with the MLA are also depicted. A percentage of diameter stenosis (% DV) is also shown. The user interface also displays an estimated FFR value of 0.78 in this embodiment.

Figure 2:
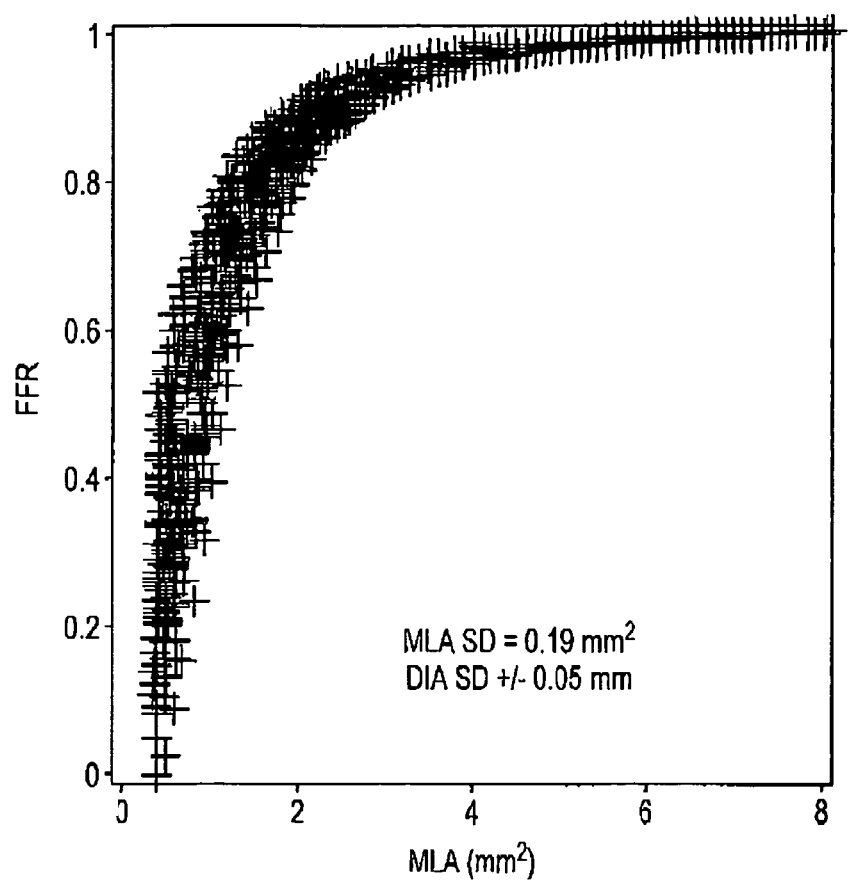
FIG. 2 is graph showing the non-linear relationship of FFR versus MLA according to an illustrative embodiment of the invention.

FIG. 2 is a plot that shows a simulation of the non-linear relationship between MLA and the calculated FFR. A review of this plot shows that as MLA increases from left to right on the x-axis, the measured FFR values that are determined using the measured MLA increase steeply and then plateau in a non-linear manner. This plot also includes a standard deviation of the MLA and diameter used to generate the graph.

Figure 3:
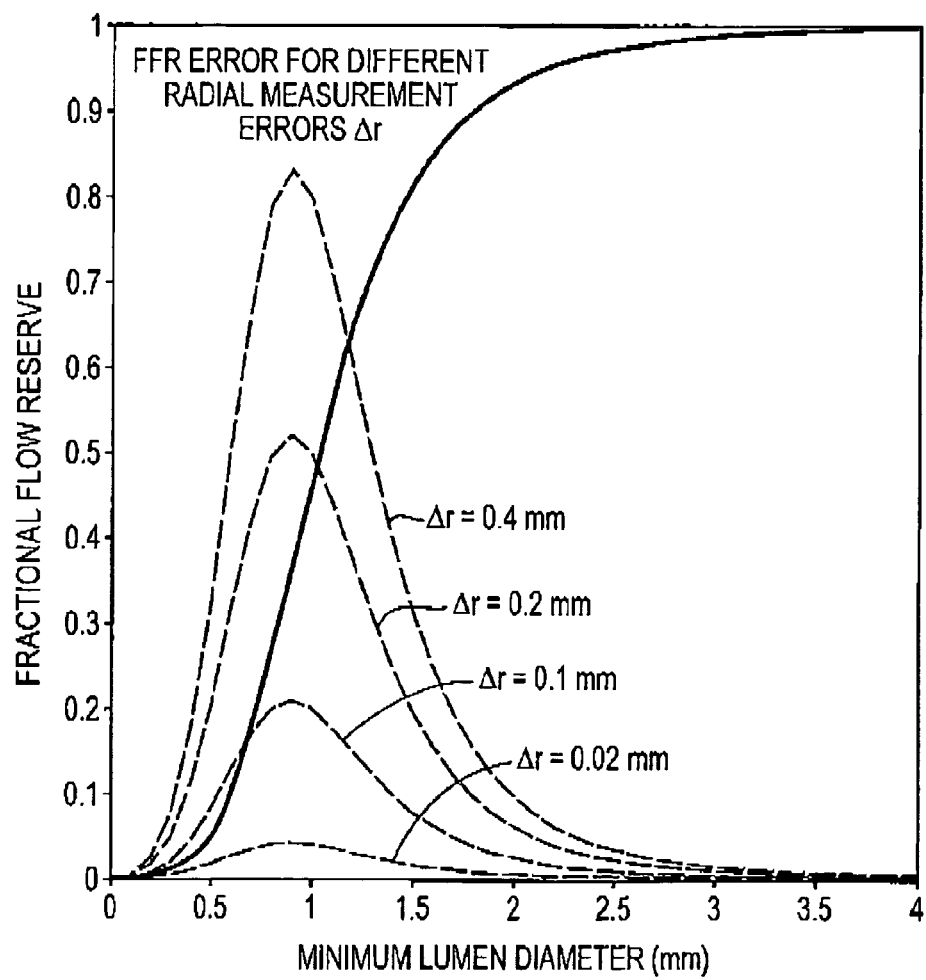
FIG. 3 is a graph of the effect of radial error in measuring diameter on FFR according to an illustrative embodiment of the invention.

FIG. 3 shows a graph of minimum lumen diameter versus FFR values. Specifically, the solid curve of FIG. 3 shows FFR changing as a function of MLA. The relationship between FFR and MLA is nonlinear. FIG. 3 also shows four curves having dotted lines that correspond to error in the FFR values plotted against MLA for four different radial error values. In turn, for each of the four dotted curves showing peaks of varying heights indicate how errors in the FFR values increase as the radial measurement errors increase from about 0.02 mm to about 0.4 mm. The measured radial values each include radial error amounts that introduce error in the lumen geometry and associated measured lumen area that are analyzed to determine the MLA. Accordingly, the error curves highlight the importance of accuracy and repeatability in the measurement of MLA as an input for determining FFR according to the models and methods described herein. Diameter measurement accuracy is important because reducing diameter measurement errors helps determine an accurate FFR value. In particular, for an FFR values that are greater than or about equal to about 0.5 and less than or about equal to about 0.8 range diameter accuracy measurements for the lumen wall are significant.

Figures 4A, 4B:
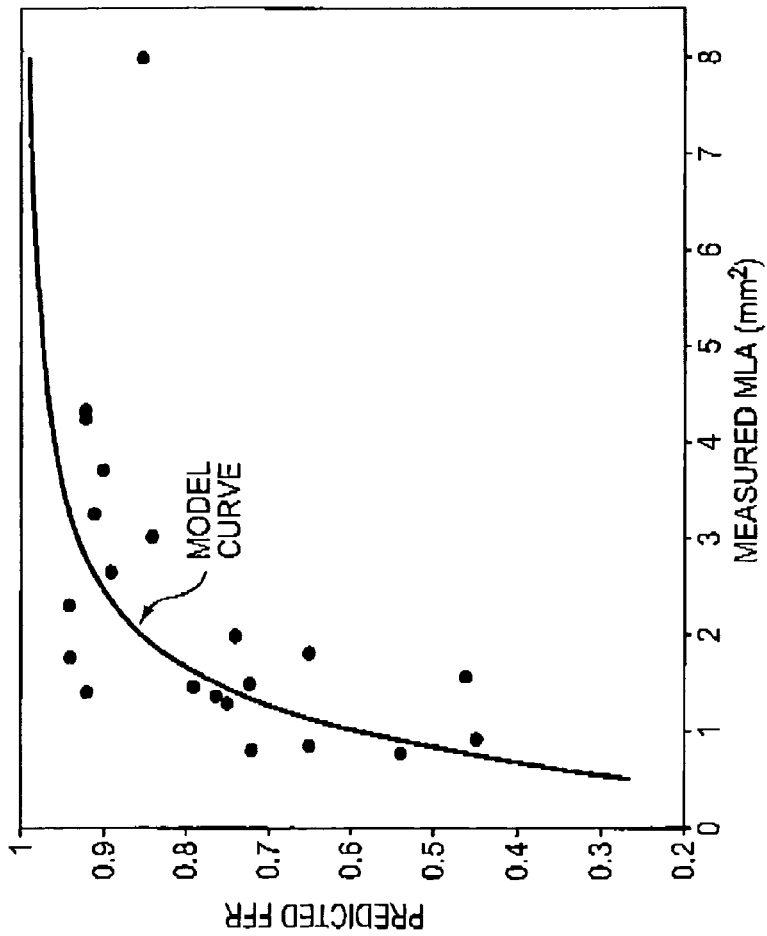
FIG. 4A is a graph of estimated FFR generated based on MLA according to an illustrative embodiment of the invention.
FIG. 4B shows one or more of the parameters and parameter relationships for the model that gives rise to the model curve plotted in FIG. 4A according to an illustrative embodiment of the invention.
Figure 5B:
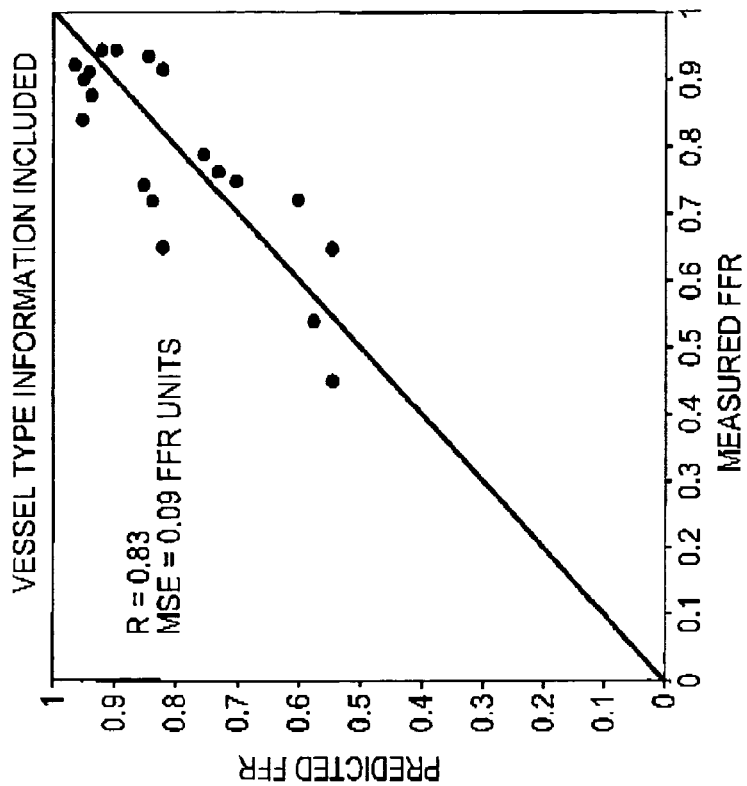
FIGS. 5A and 5B are graphs showing measured FFR compared to an estimated FFR obtained using measured MLA values obtained based upon OCT data described herein in which vessel type correction is not used (FIG. 5A), and wherein such vessel type correction is used (FIG. 5B) according to an illustrative embodiment of the invention.
Figure 5A:
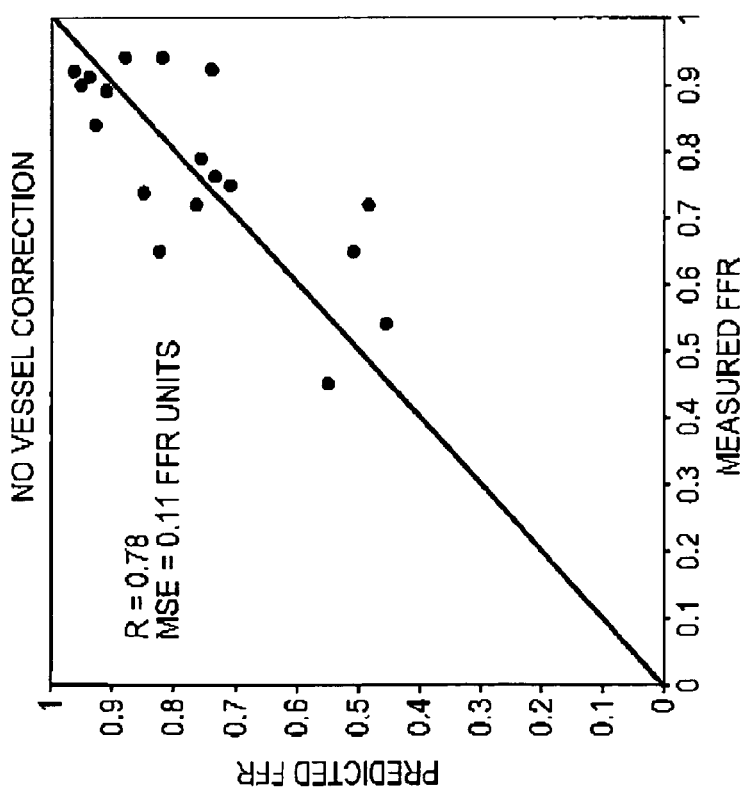

FIG. 4A shows a graph of the relationship between FFR measured using a pressure wire in patients that have coronary artery disease and corresponding measurements obtained from the same patients using an OCT data collection probe. The solid curve identified as the model curve in FIG. 4A shows the predicted relationship between FFR and MLA from Eq. 12, with k=0.683 mm$^2$ and γ=1. FIG. 4B shows one or more of the parameters and parameter relationships for the model curve in FIG. 4A. The relationship between the measured and estimated FFR values is shown in FIG. 5A for a vessel-independent value of γ and in FIG. 5B for vessel-dependent values of γ (Eq. 13). These results indicate that the disclosed methods produce MLA-derived FFR estimates that correlate linearly with FFR measurements. A comparison of FIGS. 5A and 5B indicates that the accuracy of the estimates can be improved by using different values of γ for the different types of arteries. In FIG. 5A, without the use of vessel type as a parameter, the mean square error (MSE) is about 0.11 FFR units with a R value of about 0.78. In FIG. 5B, with the use of vessel type as a parameter, the mean square error (MSE) is about 0.09 FFR units with a R value of about 0.83.

Figure 6B:
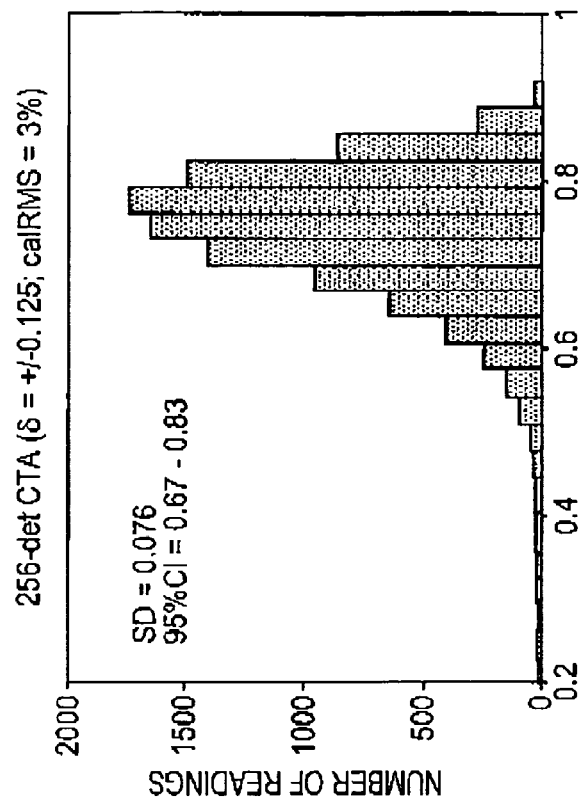
FIGS. 6A and 6B are graphs of 64-element computed tomography angiography (CTA) and 256 element CTA measured with respect to the blood vessel in which the number of readings is plotted versus FFR, respectively according to an illustrative embodiment of the invention.
Figure 6A:
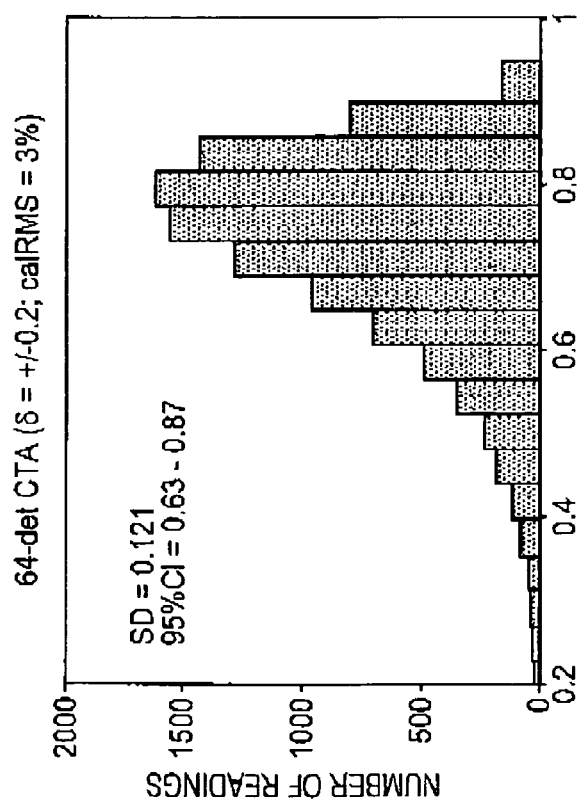
Figure 6D:
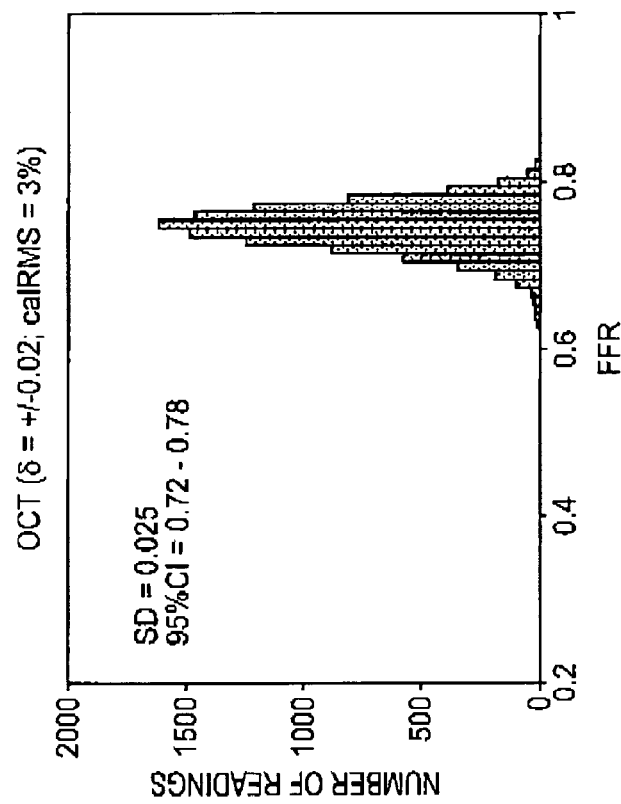
FIG. 6D is a graph of OCT data measured with respect to the blood vessel in which the number of readings is plotted versus FFR, respectively according to an illustrative embodiment of the invention.
Figure 6C:
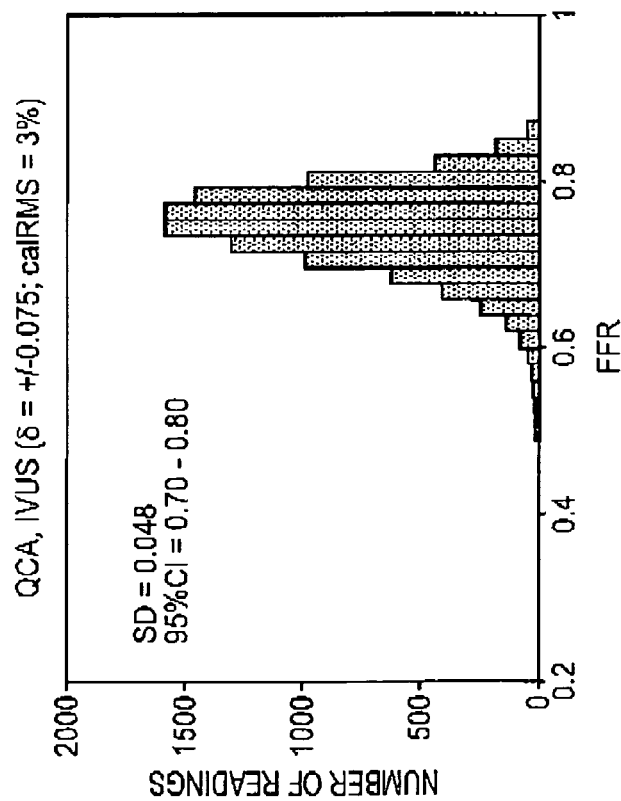
FIG. 6C is a graph of intravascular ultrasound (IVUS) or quantitative coronary analysis (QCA) data measured with respect to the blood vessel in which the number of readings is plotted versus FFR, respectively according to an illustrative embodiment of the invention.
Figures 7A, 7B:
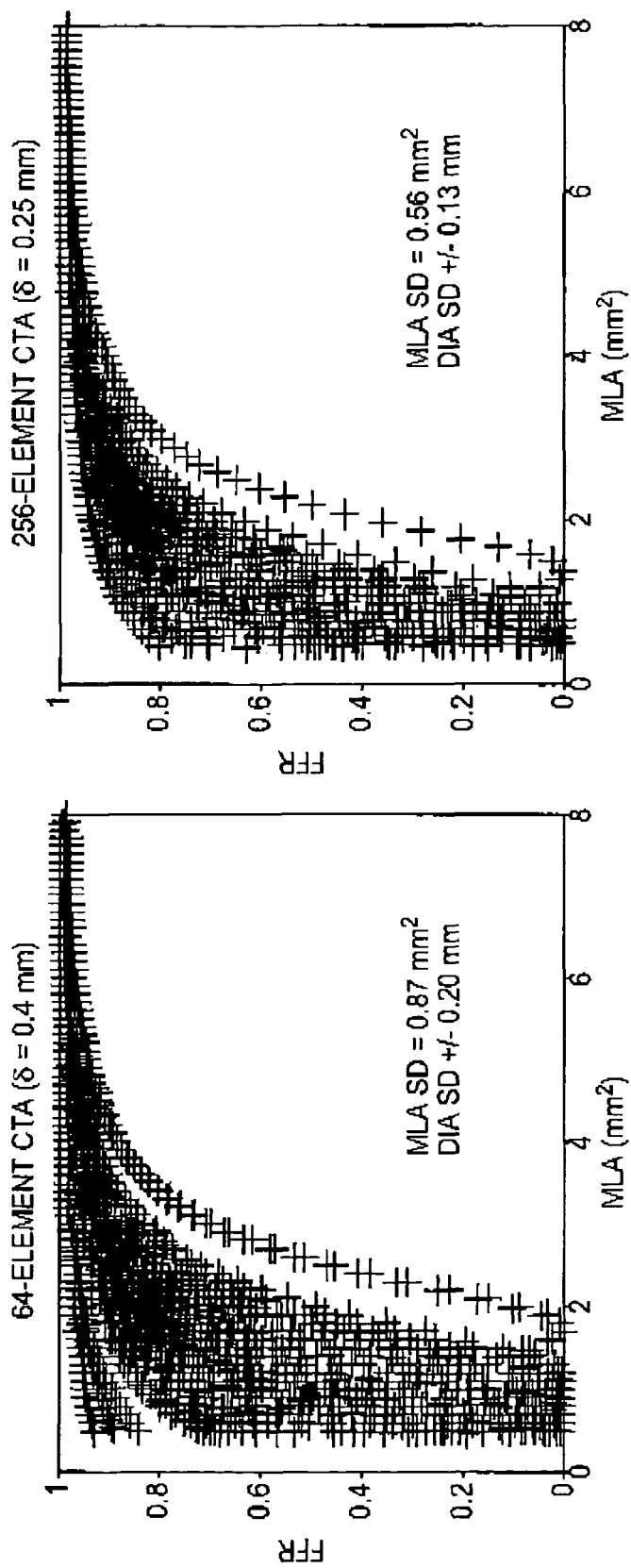
FIGS. 7A and 7B are graphs of 64-element computed tomography angiography (CTA) and 256 element CTA measured with respect to the blood vessel in which FFR is plotted relative to MLA, respectively according to an illustrative embodiment of the invention.
Figures 7C, 7D:
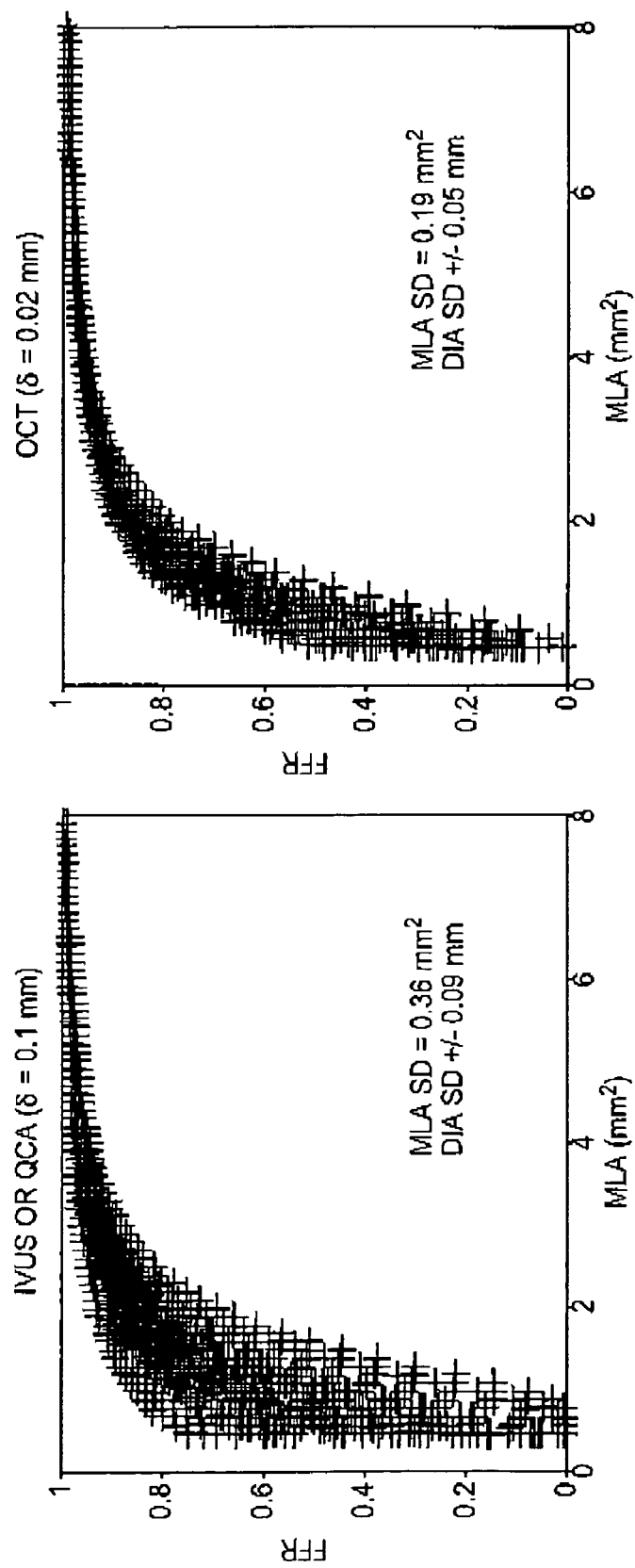
FIG. 7C is a graph of intravascular ultrasound (IVUS) or quantitative coronary analysis (QCA) data measured with respect to the blood vessel in which the number of readings is plotted versus FFR, respectively according to an illustrative embodiment of the invention.
FIG. 7D is a graph of OCT data measured with respect to the blood vessel in which the number of readings is plotted versus FFR, respectively according to an illustrative embodiment of the invention.

FIGS. 6A-6D show various plots of FFR values obtained using different data collection methods with various standard deviations (SD) and confidence intervals (CI) for a blood vessel of interest. These figures show graphs of FFR values versus the number of readings taken for different imaging modalities OCT (FIG. 6D), IVUS (FIG. 6C), 256 element CTA (FIG. 6B) and 64-element CTA (FIG. 6A). The CI for the OCT data is the narrowest and most accurate of the four data collection methods shown in FIGS. 6A-6D. The OCT-based FFR values shown in FIG. 6D were obtained using the MLA based models described herein. The data shown in FIGS. 7A-7D is based on the same data and blood vessel as used in FIGS. 6A-6D.

FIGS. 7A-7D show various plots of FFR values obtained using different data collection methods with various standard deviations (SD) and confidence intervals (CI) for a blood vessel of interest. An absolute RMS accuracy of 3% was assumed for all modalities shown in FIGS. 7A-7D. As shown in these figures, the OCT-based data in FIG. 7D has the least spread in values and shows an accurate relationship between MLA and FFR. The FFR values shown in FIGS. 7A-7D were obtained using OCT data to generate a MLA which was turn used with the models described herein.

In the description, the invention is discussed in the context of optical coherence tomography; however, these embodiments are not intended to be limiting and those skilled in the art will appreciate that the invention can also be used for other imaging and diagnostic modalities.

The terms light and electromagnetic radiation are used interchangeably herein such that each term includes all wavelength (and frequency) ranges and individual wavelengths (and frequencies) in the electromagnetic spectrum. Similarly, the terms device and apparatus are also used interchangeably. In part, embodiments of the invention relate to or include, without limitation: sources of electromagnetic radiation and components thereof; systems, subsystems, and apparatuses that include such sources; mechanical, optical, electrical and other suitable devices that can be used as part of or in communication with the foregoing; and methods relating to each of the forgoing. Accordingly, a source of electromagnetic radiation can include any apparatus, matter, system, or combination of devices that emits, re-emits, transmits, radiates or otherwise generates light of one or more wavelengths or frequencies.

One example of a source of electromagnetic radiation is a laser. A laser is a device or system that produces or amplifies light by the process of stimulated emission of radiation. Although the types and variations in laser design are too extensive to recite and continue to evolve, some non-limiting examples of lasers suitable for use in embodiments of the invention can include tunable lasers (sometimes referred to as swept source lasers), superluminescent diodes, laser diodes, semiconductor lasers, mode-locked lasers, gas lasers, fiber lasers, solid-state lasers, waveguide lasers, laser amplifiers (sometimes referred to as optical amplifiers), laser oscillators, and amplified spontaneous emission lasers (sometimes referred to as mirrorless lasers or superradiant lasers).

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Non-Limiting Software Embodiments for Implementing Software and Processor Based Processes or Models The present invention may be embodied in may different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system.

In one embodiment of the present invention, some or all of the processing of the data used to generate, determine or output a FFR value is implemented as a set of computer program instructions that is converted into a computer executable form, stored as such in a computer readable medium, and executed by a processor such as a microprocessor under the control of an operating system. Thus, query response and input data are transformed into processor understandable instructions suitable for generating OCT data, OCT images, vascular resistance, fractional flow reserve, overlay masks, area detection, correlating reference data with new data, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed over a network.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, systems of equations, areas, flow reserves, MLAs, FFRs, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

What is claimed:

1. A processor-based method of determining an estimated fractional flow reserve (FFR) comprising:
   collecting optical coherence tomography (OCT) image data from a lumen of a blood vessel while pulling an OCT probe through the lumen;
   determining, using a processor and the OCT image data, a location of a stenotic lesion in the blood vessel;
   determining, using the processor and the OCT image data, the minimum lumen area (MLA) at the stenotic lesion location; and
   calculating, using the processor and a software-based model, the estimated FFR,
   wherein the software-based model determines the estimated FFR using the following relationship:

estimated $FFR=(\text{MLA value})^2/[(\text{MLA value})^2+k]$,
   wherein $k$ is constant.

2. The processor-based method of claim 1 wherein the constant k is empirically determined and describes an error value.

3. The processor-based method of claim 1 wherein k ranges from 0.5 mm² to 0.7 mm².

4. A processor-based method of determining an estimated fractional flow reserve (FFR) comprising:
   collecting optical coherence tomography (OCT) data from a lumen of a blood vessel while pulling an OCT probe through the lumen;
   determining, using a processor, a location of a stenotic lesion in the blood vessel;
   determining, using the processor, the minimum lumen area (MLA) at the stenotic lesion location;
   calculating, using the processor and a software-based model, the estimated FFR,
   wherein the software-based model determines the estimated FFR using the following relationship:

estimated $FFR=[\gamma(\text{MLA value})^2]/[\gamma(\text{MLA value})^2+k]$,
   wherein $\gamma$ is a blood vessel type specific parameter; and displaying the estimated FFR.

5. The processor-based method of claim 1 further comprising the steps of:
   generating a plurality of images based on the OCT data, each image corresponding to a cross-section of the blood vessel; and
   determining a luminal border for one or more of the plurality of images, wherein the MLA is determined using the luminal border.

6. The processor-based method of claim 1 further comprising the step of configuring the software-based model such that hyperemic flow is constant.

7. The processor-based method of claim 1, wherein resistance to flow in the stenotic lesion, as used in the software-based model, is configured to be k/(MLA value).

8. The processor-based method of claim 1, wherein the processor is further configured to generate an output that indicates a stenotic lesion is present in the blood vessel if the estimated FFR is 0.80 or less.

9. The processor-based method of claim 4, wherein $\gamma$ ranges from 1.0 mm² to 2.0 mm².

10. The processor-based method of claim 1, wherein a ratio of D/L is constant, wherein L is the length of a stenotic lesion and D is a diameter of the blood vessel outside of the stenotic lesion.

11. The processor-based method of claim 1, wherein $A^2/(\text{MLA value})^2>1$, wherein A is an area of the blood vessel outside of the stenotic lesion.

12. The processor-based method of claim 6, wherein a ratio of D/L is constant, wherein L is the length of a stenotic lesion and D is a diameter of the blood vessel outside of the stenotic lesion.

13. The processor-based method of claim 6, wherein $A^2/(\text{MLA value})^2>1$, wherein A is an area of the blood vessel outside of the stenotic lesion.

* * * * *